US008518037B2

(12) United States Patent
Young (10) Patent No.: US 8,518,037 B2
(45) Date of Patent: Aug. 27, 2013

(54) RADIOFREQUENCY ABLATION DEVICE

(75) Inventor: Kimbolt Young, Newtonville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 737 days.

(21) Appl. No.: 12/260,003

(22) Filed: Oct. 28, 2008

(65) Prior Publication Data

US 2009/0112201 A1 Apr. 30, 2009

Related U.S. Application Data (60) Provisional application No. 60/983,914, filed on Oct. 30, 2007.

(51) Int. Cl.
*A61B 18/04* (2006.01)
*A61B 18/18* (2006.01)
*A61N 1/00* (2006.01)

(52) U.S. Cl.
USPC .................... 606/41; 606/33; 607/148

(58) Field of Classification Search
USPC ............ 606/32, 41, 49, 50; 607/98, 99, 607/113, 115, 116, 128, 148
See application file for complete search history.

(56) References Cited

U.S. PATENT DOCUMENTS

| 3,174,851 | A | | 3/1965 | Buehler et al. |
| 3,351,463 | A | | 11/1967 | Rozner et al. |
| 3,753,700 | A | | 8/1973 | Harrison et al. |
| 6,050,992 | A | * | 4/2000 | Nichols ........................... 606/41 |
| 6,217,554 | B1 | * | 4/2001 | Green ........................ 604/164.01 |
| 2004/0153057 | A1 | | 8/2004 | Davison |
| 2007/0161977 | A1 | | 7/2007 | Moorman et al. |

FOREIGN PATENT DOCUMENTS

WO   WO 2006095171 A1 *   9/2006

OTHER PUBLICATIONS

Jaskolka, Jeffrey D., Needle Tract Seeding after Radiofrequency Ablation of Hepatic Tumors, J Vasc Interv Radiol 2005; 16:485-491.

* cited by examiner

*Primary Examiner* — Nicholas Lucchesi
*Assistant Examiner* — Nathan R Price
(74) *Attorney, Agent, or Firm* — Bingham McCutchen LLP (57) ABSTRACT

A radiofrequency ablation device includes an elongate cannula having a distal portion and a proximal portion and a lumen extending between the distal and proximal portions. The RF ablation device further includes an elongate tubular member disposed within the lumen of the elongate cannula, the elongate tubular member having a distal region and a proximal region, the elongate tubular member including a lumen extending between the distal and proximal portions. A sildable electrode member is disposed in the portion of the elongate cannula lumen located external to the elongate tubular member. As an alternative to the elongate tubular member, the electrode member may include a lumen. The lumen of the elongate tubular member (or electrode member) carries or vents gaseous vapor generated during the RF ablation process.

12 Claims, 6 Drawing Sheets

RADIOFREQUENCY ABLATION DEVICE

RELATED APPLICATION

This Application claims priority to U.S. Provisional Patent Application No. 60/983,914 filed on Oct. 30, 2007. The above-noted Application is incorporated by reference as if set forth fully herein.

FIELD OF THE INVENTION

The field of the invention generally relates to the structure and use of radio frequency (RF) electrosurgical probes or ablation devices for the treatment of tissue.

BACKGROUND OF THE INVENTION

In the field of oncology, cancer treatment is often performed using radio frequency (RF) ablation techniques. Conventional ablation techniques use an array of RF needles or tines (sometimes referred to as a "tine array"), which may be configured to deploy in a pre-determined shape or pattern for transferring RF energy into surrounding tissue. The needles or tines act as electrodes which are electrically connected to a RF generator. The needles or tines thus transmit RF energy into the surrounding tissue for the thermal coagulation and/or necrosis of tissue. For example, in an undeployed state, tines are positioned at a target area while housed within the lumen of a cannula. The undeployed tine array enclosed within the cannula may be positioned by inserting the cannula through bone and tissue into a target area. Once inserted, the electrode tine array may be deployed by forcing the electrode tines out of a cannula and into the surrounding target tissue. After deployment, RF energy may be transmitted from the electrode tine array to ablate the target tissue, causing heating and eventual necrosis of cancerous or malignant tissue. RF ablation occurs when a high frequency alternating current flows from one electrode to another, completing a current path, causing ionic agitation. Ionic agitation occurs around an active electrode as a result of frictional heating in the tissue surrounding the electrode tines (e.g., electrodes, RF needle probes, and the like) on an array, leading to cell death and necrosis. After ablating the target tissue, the electrode tine array is then retracted into the cannula and the cannula is removed from the target area.

RF ablation probes may be configured in either monopolar or bipolar mode. In monopolar mode, one electrode (e.g., negative) is located within or on a cannula. In order to complete the circuit for RF energy, a separate electrode pad or the like is typically placed on the skin of the patient. Other bipolar-based devices use multiple electrodes or electrode arrays on a single device. For example, the CONCERTO™ needle electrode device (Boston Scientific Scimed, Inc., Maple Grove, Minn.) uses two electrically independent opposing arrays that are contained within an insulated cannula. RF energy passes between the two arrays and heats the tissue surrounding and in between the arrays.

In one known arrangement, the electrode array may be deployed via a distal end of the cannula. Once the electrode array is deployed and activated, RF energy heats the tissue to an elevated temperature so as to ablate and ultimately kill the cancerous tissue. During the ablation process, the pressure inside the tumor (e.g., intra-tumoral pressure) increases due to the heating of moisture within the tissue above its boiling point. Small or localized region(s) within the tumor may include gaseous pockets of heated moisture which leads to a "popping" effect. The popping is caused when the gaseous moisture created within the affected tissue cannot escape readily to the ambient environment and consequently builds up with the tissue until it is liberated in a sudden release. The popping phenomena is of great concern because it is suspected that the popping process may contribute to tumor seeding. For example, cancerous cells may be forcibly expelled or moved during the popping phenomena and become lodged in healthy tissue at which point the cancer may return or spread.

A secondary concern with popping relates to patient comfort. During many percutaneous RF procedures, the subject is consciously sedated during the ablation procedure. The popping of tissue during the application of RF energy to the tissue can be painful to the subject. The popping sound may also be heard by the patient, thereby raising anxiety and discomfort during the procedure.

There thus is a need for a RF ablation device that is able to minimize or eliminate the popping effect that accompanies RF ablation of tissue. Such a device would increase patient comfort as well as reduce the chances of tumor seeding.

SUMMARY

In one embodiment of the invention, a radiofrequency ablation device includes an elongate cannula having a distal portion and a proximal portion and a lumen extending between the distal portion and the proximal portion. The RF ablation device further includes an electrode member slidably disposed in elongate cannula lumen, the electrode member including a lumen extending between a distal portion and a proximal portion. The lumen provides a passageway or channel to vent gaseous components liberated during the RF ablation process.

In another embodiment of the invention, a radiofrequency ablation device includes an elongate cannula having a distal portion and a proximal portion and a lumen extending between the distal portion and the proximal portion. The RF ablation device further includes an elongate tubular member disposed within the lumen of the elongate cannula, the elongate tubular member having a distal region and a proximal region, the elongate tubular member including a lumen extending between the distal portion and the proximal portion thereof. A sildable electrode member is disposed in the portion of the elongate cannula lumen located external to the elongate tubular member. The electrode member includes a plurality of tines at the distal portion thereof, the plurality of tines being configured to deploy from the elongate cannula as the electrode member is moved toward the distal portion of the elongate cannula. The lumen of the elongate tubular member carries or vents gaseous vapor generated during the RF ablation process.

In another embodiment, a method of treating tissue with a radiofrequency ablation device includes positioning a radiofrequency ablation device within a tumor located in a subject. The radiofrequency ablation device includes an elongate tubular member disposed along a length thereof. Alternatively, the elongate tubular member is omitted and a lumen of the electrode member is used to vent gases. The elongate tubular member (or electrode member) includes a lumen therein extending from the tumor to a location external to the subject. The radiofrequency ablation device is then activated so as to heat the tumor, wherein the activation generates vapor within at least a portion of the tumor. At least a portion of the vapor is vented via the lumen of the elongate tubular member or electrode member.

In still another embodiment of the invention, a method of treating tissue with a radiofrequency ablation device includes positioning a radiofrequency ablation device within a tumor located in a subject, the radiofrequency ablation device including an lumen extending from a distal end to a proximal end. The lumen may be located in an elongate tubular member disposed along a length thereof or in an electrode member. A removable stylet is provided and configured for placement within the lumen of the elongate tubular member or the electrode member. The stylet is then withdrawn or removed from the lumen of the elongate tubular member/electrode member and the radiofrequency ablation device is activated so as to heat the tumor, wherein the activation generates vapor within at least a portion of the tumor. At least a portion of the vapor is vented via the lumen. The stylet may be removed before application or RF energy or during the application of RF energy.

In both the methods described above, the vapor may be vented to the atmosphere or it may be filtered or passed into a collection device such as a container or the like. The lumen of the elongate tubular member/electrode member may also be used to deliver fluids and other materials to the site of interest. The lumen of the elongate tubular member or electrode member may also act as a conduit that rides along the length of a guiding needle.

BRIEF DESCRIPTION OF THE DRAWINGS

The drawings illustrate the design and utility of various embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION

Figure 1:
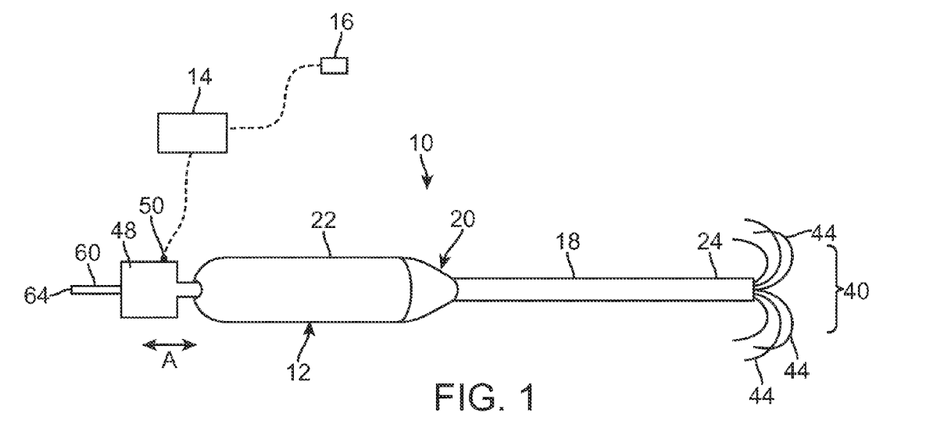
FIG. 1 is a schematic representation of a tissue ablation system according to one aspect of the invention.

FIG. 1 illustrates a radiofrequency (RF) ablation device 10 according to one embodiment of the invention. As seen in FIG. 1, the RF ablation device 10 includes probe assembly 12 that is configured for introduction into a body of a patient for ablative treatment of target tissue. The target tissue may include, for example, diseased or cancerous tissue located within an organ or body tissue. As one illustrative example, the RF ablation device 10 may be used to ablate cancerous tissue located within liver tissue although the invention is not limited to the type of tissue being ablated. The RF ablation device 10 is coupled to a RF generator 14 configured for supplying RF energy to the probe assembly 12 in a controlled manner.

The RF generator 14 typically uses impedance-based feedback designed to accurately monitor the extent and nature of tissue desiccation to accommodate lesion and patient variability. The RF generator 14 is also coupled to an electrode pad 16 as illustrated in FIG. 1. The electrode pad 16 acts as a return electrode during activation of RF ablation device 10. Of course, the probe assembly 12 described herein may also include so-called bipolar devices in which case the electrode pad 16 is not utilized. One exemplary RF generator 14 that may be used in connection with the RF ablation device 10 is the RF 3000 Generator sold by Boston Scientific Corporation, Natick, Mass.

The probe assembly 12 as seen in FIG. 1, includes an elongate cannula 18 that is coupled at a proximal end 20 to a handle 22 or the like that is used to grip the device 10. The elongate cannula 18 may terminate in a sharpened or blunted distal tip 24. The elongate cannula 18 may have a rigid construction such that the device 10, when inserted into a target tissue, does not torque, bend, or flex. The elongate cannula 18 may be constructed of a metallic material such as, for example, stainless steel, titanium, NITINOL, or the like. In another aspect, a rigid or stiff polymer or plastic material may be used to construct the elongate cannula 18. The invention is not limited to the type of material used to form the elongate cannula 18. Typically, the elongate cannula 18 is coated or covered with an insulative material. The elongate cannula 18 may also have a number of markers or gradations disposed along all or a portion of its length. The markers may be formed from a radiopaque paint or other material such that the physician is able to view the location of the elongate cannula 18 during the procedure using appropriate visualization (e.g., ultrasound (US) or computed tomography (CT) techniques).

The cannula 18 may have a suitable length such that the array of electrodes 40 can be positioned to the target region or zone of interest. Typically, the cannula 18 may have a length in the range of around 5 cm to 30 cm although other lengths are contemplated to fall within the scope of the invention. The outer or external wall of the cannula 18 may have an outside, cross-sectional dimension that is consistent with its intended use. For example, the cannula 18 may have an outer diameter (O.D.) within the range of about 0.058 inches (17 gage) to about 0.134 inches (10 gage) although other outer diameters outside this range are also contemplated.

Figure 2:
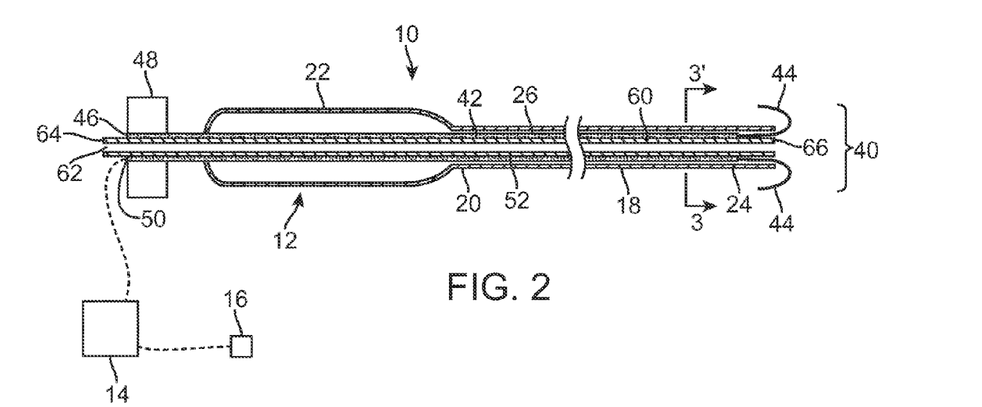
FIG. 2 is cross-sectional view of a RF ablation probe device according to one aspect of the invention.

As best seen in FIG. 2, the cannula 18 includes a lumen 26 that extends from the distal tip 24 and through the handle 22. The lumen 26 is sized to hold the slidable electrode member 42 along with the elongate tubular member 60 which are described in more detail herein. The inner surface of the lumen 26 may be coated with a lubricious coating to reduce the friction between the slidable electrode member 42 and the cannula 18. The distal end of the slidable electrode member 42 terminates in an electrode array 40. The array 40 is formed from a plurality of electrode tines 44, each of which resembles the shape of a needle or wire. Each tine 44 may be in the form of a slender metal element, which can penetrate into tissue as it is advanced to a target site within the target region. In some embodiments, the distal ends of the tines 44 may be honed or sharpened to facilitate their ability to penetrate tissue. The distal ends of these electrode tines 44 may be hardened using conventional heat treatment or other metallurgical processes. They may be partially covered with insulation, although they will be at least partially free from insulation over their distal portions so as to effectuate tissue heating and ablation.

When deployed from the cannula 18, the electrode array 40 has a deployed configuration that defines a volume having a periphery with a radius in the range from around 0.5 cm to around 4.0 cm. It should be understood, however, that other geometries and dimensions are contemplated to fall within the scope of the invention. The array of electrode tines 44 are resilient and may be pre-shaped or biased to assume a desired configuration when advanced into a target tissue or region of tissue. In the illustrated embodiments, the electrode tines 44 diverge radially outwardly from the cannula 18 in a uniform pattern, i.e., with the spacing between adjacent electrodes tines 44 diverging in a substantially uniform and/or symmetric pattern. The electrodes tines 44 should not be limited to having the profiles shown in FIGS. 1, 2, and 4-7 and that, in alternative embodiments, the electrode tines 44 can have different deployed profiles. In certain embodiments, the deployed array 40 may even have a non-symmetrical orientation. It should be noted that although a total of six (6) electrodes tines 44 are illustrated, for example, in FIGS. 1 and 4-6, in other embodiments, the probe assembly 12 can have any number of electrode tines 44.

The electrode tines 44 can be made from a variety of electrically conductive elastic materials. Very desirable materials of construction, from a mechanical point of view, are materials which maintain their shape despite being subjected to high stress. Certain "super-elastic alloys" include nickel/titanium alloys, copper/zinc alloys, or nickel/aluminum alloys. Alloys that may be used are also described in U.S. Pat. Nos. 3,174,851, 3,351,463, and 3,753,700, the disclosures of which are hereby expressly incorporated by reference. The electrode tines 44 may also be made from any of a wide variety of stainless steels. The electrode tines 44 may also include the platinum group metals, especially platinum, rhodium, palladium, rhenium, as well as tungsten, gold, silver, tantalum, and alloys of these metals. These metals are largely biologically inert. They also have significant radiopacity to allow the electrode tines 44 to be visualized in-situ, and their alloys may be tailored to accomplish an appropriate blend of flexibility and stiffness. They may be coated onto the electrode tines 44 or be mixed with another material used for their construction.

The electrode tines 44 may be electrically bonded or otherwise joined to the distal end of the slidable electrode member 42. For example, the electrode tines 44 may be soldered to the end of the electrode member 42. Alternatively, the electrode tines 44 may be formed directly from a unitary element forming the electrode member 42. For example, the electrode member 42 may be formed as a tube or the like that include a plurality of slots formed in the distal end to create the individual electrode tines 44. As one illustrative example, the electrode member 42 may include an outer hollow tubular member (e.g., steel hypotube) that is coupled at a distal end to a proximally arranged electrode array 40.

Still referring to FIG. 2, the slidable electrode member 42 includes a proximal end 46 that is disposed proximally with respect to the handle 22. The slidable electrode member 42 is moveable in the direction or arrow A in FIG. 1. The slidable electrode member 42 may be affixed to a hub 48. The hub 48 may be made from an electrically non-conductive material and is grasped by the user of the probe assembly 12 to slide the electrode member 42 and electrode tines 44 relative to the elongate cannula 18 in the proximal/distal direction of arrow A. The hub 48 may include an electrical connector 50 as illustrated in FIG. 1 that is used to connect the RF generator 14. While the embodiments of FIGS. 1, 2, and 4-7 illustrate axial movement of the hub 48 to deploy the electrode tines 44, in an alternative configuration a twisting or rotation motion of a hub 48 may be used to deploy and retract the electrode tines 44.

The slidable electrode member 42 may include a hollow interior portion or lumen 52 that extends from the proximal end 46 to the beginning of the electrode tines 44. As seen in FIG. 2, an elongate tubular member 60 is disposed within the lumen of the slidable electrode member 42. In this regard, a concentric arrangement between the slidable electrode member 42 and the elongate tubular member 60 is used with the elongate tubular member 60 acting as a center mandrel. The elongate tubular member 60 may be formed as an elongate tube, conduit, channel or the like and includes a lumen 62 therein that extends from the proximal end 64 to the distal end 66. The length of the elongate tubular member 60 may vary but is shown in FIG. 2 as extending proximally with respect to the hub 48.

The elongate tubular member 60 may be formed a number of materials including, for example, stainless steel, titanium, NITINOL, electrically conductive composite materials, or a combination of composite material and metal. Examples include ICONEL, ABS, NYLON (PTFE), and ULTEM. The elongate tubular member 60 may be electrically isolated from the slidable electrode member 42 using, for example, an insulating layer interposed between the two. The elongate tubular member 60 may be optionally annealed to provide malleability to angle or shape the elongate tubular member 60 into the desired shape or configuration. In this regard, the elongate tubular member 60 may be straight, angular, or curved depending on the application. For example, while FIGS. 1, 2, and 4-7 illustrate probe assemblies 12 having a straight configuration, the probe assemblies 12 may have a number of different configurations depending on their particular application.

In one embodiment of the invention, the elongate tubular member 60 is fixed relative to the outer electrode member 42. That is to say that as the slidable electrode member 42 is moved in the proximal or distal directions, the elongate tubular member 60 also moves. This may be accomplished by frictional engagement between the elongate tubular member 60 and the electrode member 42 or by bonding the elongate tubular member 60 to the electrode member 42. The elongate tubular member 60 may be directly bonded to the electrode member 42 or, alternatively, an intermediate adhesive or other layer by be used to secure the two components to one another.

Figure 12:
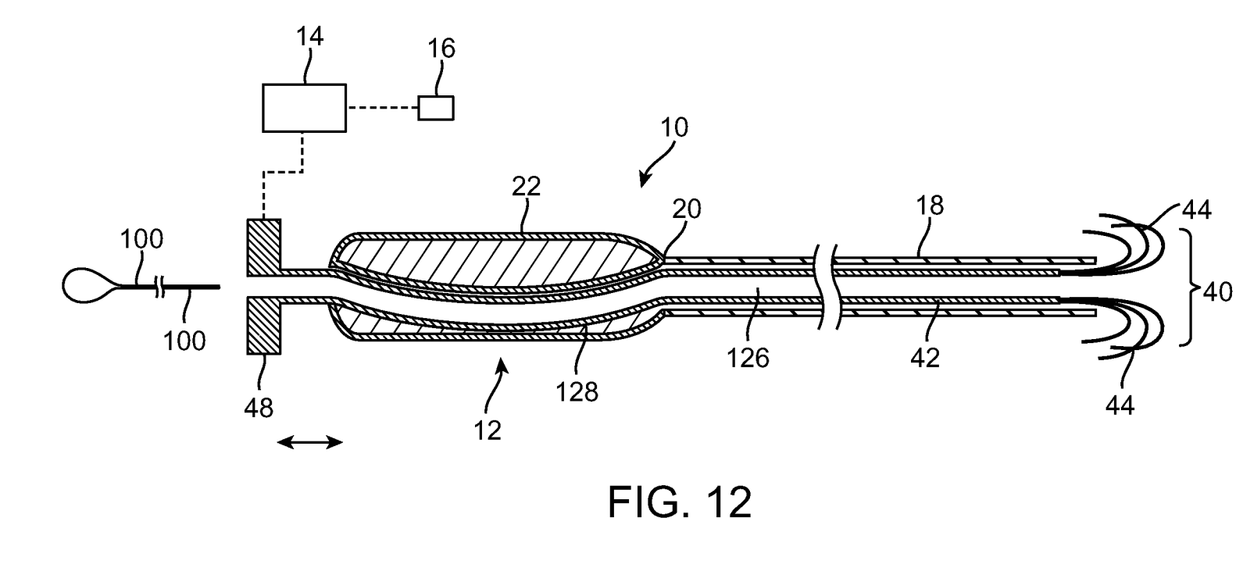
FIG. 12 illustrates a cross-sectional view of a RF ablation probe device according to one aspect of the invention.

In still other embodiments, such as that disclosed in FIG. 12, the elongate tubular member 60 is omitted entirely. In this embodiment, the electrode member 42 itself includes a lumen 126 or channel that permits the venting of vapor/pressure from the ablated tissue. This alternative embodiment avoids the need of having a second, separate tube or channel located with the cannula 18.

Figure 3:
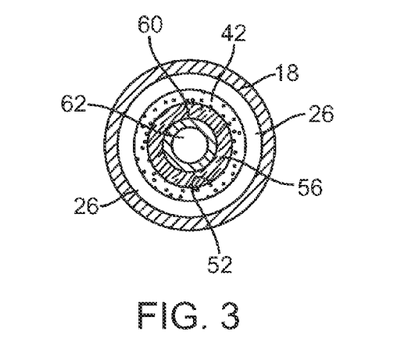
FIG. 3 is a cross-sectional view of the cannula taken along the line 3-3' of FIG. 2.

FIG. 3 illustrates a cross-sectional view of the cannula 18 of FIG. 2. Located inside the cannula 18 is the electrode member 42. While FIG. 3 illustrates a gap or tolerance between the inner surface of the cannula 18 and the electrode member 42, the construction may be such that the inner electrode member 42 physically touches or slides against the inner surface of the cannula 18. FIG. 3 further shows the electrode member 42 concentrically mounted about the elongate tubular member 60. In FIG. 3, the elongate tubular member 60 is fixed to the electrode member 42 via bonding layer 56. The bonding layer 56 may include solder, adhesive, or the like. FIG. 3 further illustrates the lumen 62 of the elongate member 60 being unobstructed or open. As explained below, this feature permits the venting of gaseous pressure that develops within the tumor during application of RF energy via the electrode array 40.

During use of the RF ablation device 10, the probe assembly is inserted into a subject to place the distal tip or end at the desired location within the subject's diseased tissue (i.e., tumor). The electrode array 40 is then deployed by moving the hub 48 distally with respect to the probe assembly 12. This causes the deployment of the electrode tines 44 from the cannula 18 and into the tumor tissue. Radiofrequency energy is then supplied to the tumor via the RF generator 14. The RF energy causes localized heating of the tumor tissue. As the heating process progresses, portions of the tissue will be heated at or above the boiling point of water (generally 100° C.). Gaseous water vapor is thus formed within the tumor tissue. The formation of gaseous vapor within the tumor is generally known to increase the intra-tumoral pressure of the tumor which, as explained in the background section, leads to unwanted popping.

The probe assembly 12 solves this problem by use of the elongate tubular member 60 to vent or shunt the gaseous vapor outside the tumor. The elongate tubular member 60 includes a central lumen 62 through which the gaseous vapor is able to pass. The excess pressure that is typically generated within the tumor is thus vented or shunted to another location that is external to the patient. In this regard, seeding of tumor cells is reduced because any entrained or carried cancerous cells or cellular material is safely sequestered from healthy tissue as the same passes through the elongate tubular member 60 of the probe assembly 12.

In one embodiment of the probe assembly 12, the elongate tubular member 60 vents directly to the ambient atmosphere. FIGS. 1 and 2, for instance, illustrate this type of venting where the lumen 62 located at the proximal end 64 of the elongate tubular member 60 vents directly to the atmosphere. Of course, tubing or other conduits may be attached to the proximal end 64 of the elongate tubular member 60 that then lead to the atmosphere.

Figure 4:
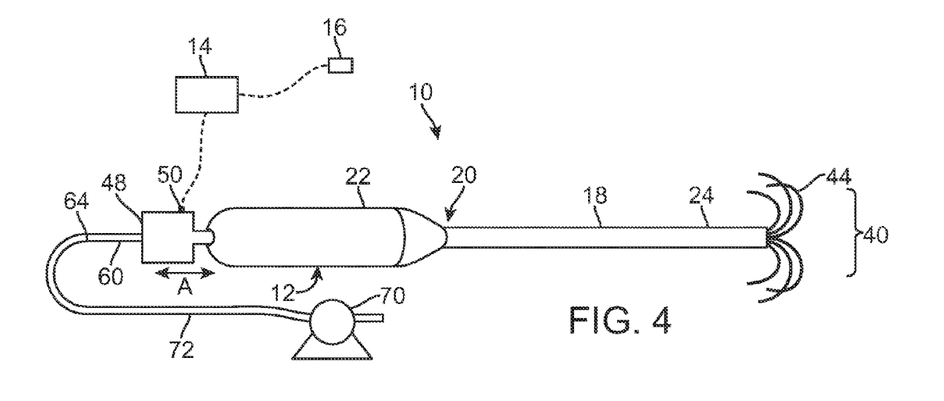
FIG. 4 is a schematic representation of a tissue ablation system according to another aspect of the invention.

FIG. 4 illustrates an alternative embodiment in which the lumen 62 of the elongate tubular member 60 is coupled to a negative pressure source 70 via a conduit 72 such as tubing or the like. The negative pressure source 70 is used to assist the venting of excess pressure created within the tumor during the RF ablation process. The negative pressure source 70 may include, for example, a pump, a low pressure chamber or the like. The negative pressure source 70 may also include a syringe or the like that is coupled to the conduit 72 to create a lower pressure within the lumen 62 to aid in withdrawing the vaporous gas created within the tumor.

Figure 5:
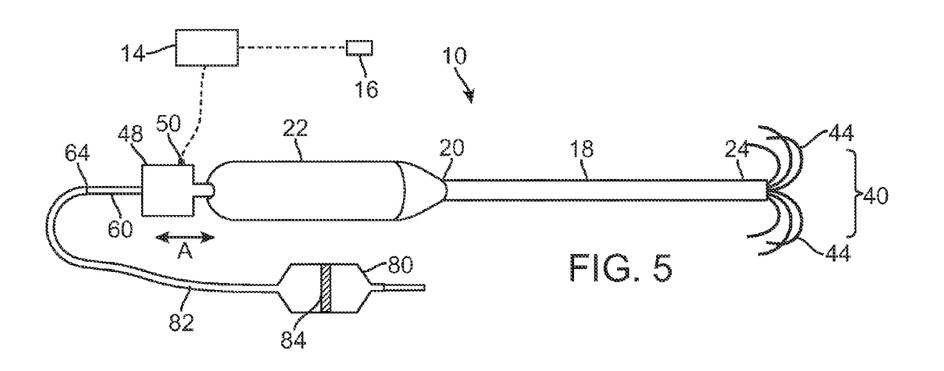
FIG. 5 is a schematic representation of a tissue ablation system according to still another aspect of the invention.

FIG. 5 illustrates another embodiment of the probe assembly 12 in which a filter 80 is connected inline with the lumen 62 of the elongate tubular member 60. Here the filter 80 is coupled to a conduit 82 such as tubing or the like. The filter 80 includes a filter medium 84 that permits passage of certain constituents of the vented gaseous vapor produced during ablation (e.g., water vapor) while not permitting passage of larger particulate matter (e.g., cells and cellular matter). In the probe assembly 12 of FIG. 5, the filter 80 may optionally be coupled to a negative pressure source 70 like that illustrated in FIG. 4. In still another aspect, the filter 80 may be disposed inside the lumen 62 of the elongate tubular member 60.

Figure 6:
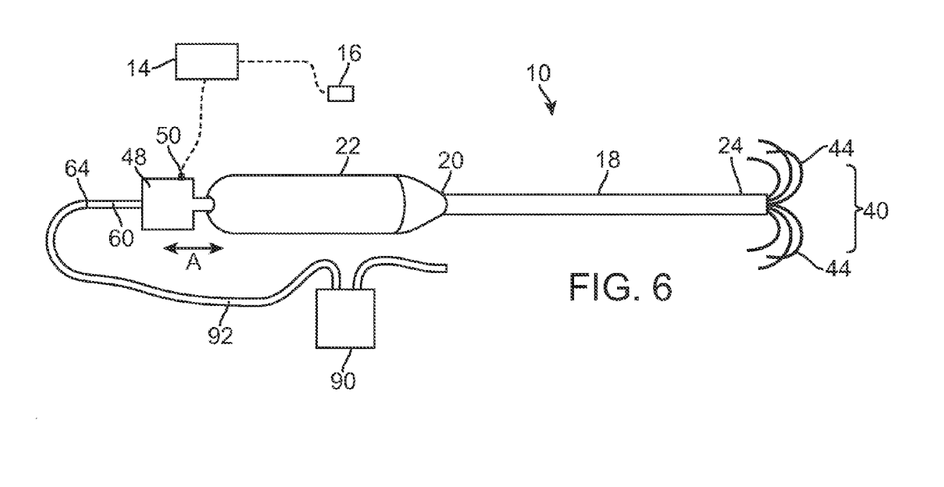
FIG. 6 is a schematic representation of a tissue ablation system according to yet another aspect of the invention.

FIG. 6 illustrates still another alternative embodiment in which a container 90 is connected inline with the lumen 62 of the elongate tubular member 60. As seen in FIG. 6, the container 90 is coupled to a conduit 92 such as tubing or the like. The container 90 is used to sequester or trap cellular matter and other debris that is vented through the lumen 62 of the elongate tubular member 60. The container 90 may optionally be coupled to a negative pressure source 70 like that illustrated in FIG. 4.

Figures 7, 8:
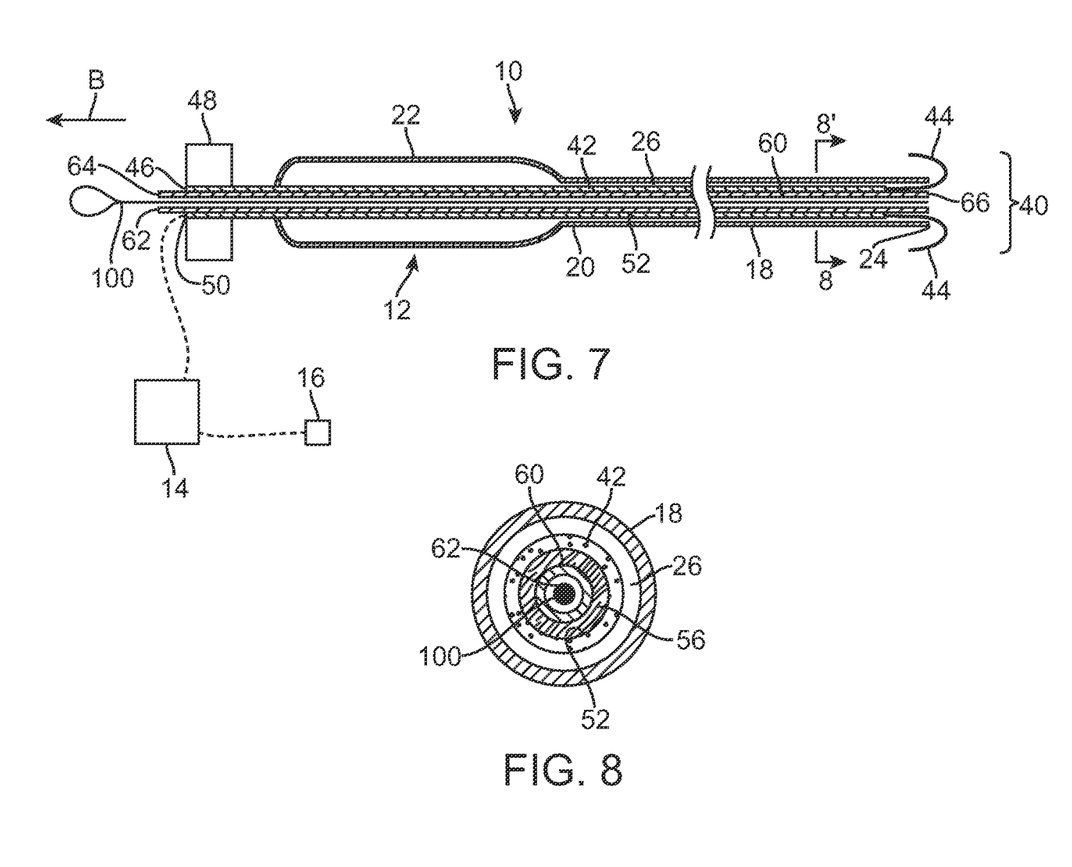
FIG. 7 is cross-sectional view of a RF ablation probe device according to another embodiment of the invention. In this embodiment, a removable stylet is shown disposed in the lumen of the elongate tubular member.
FIG. 8 is a cross-sectional view of the cannula taken along the line 8-8' of FIG. 7.

FIG. 7 illustrates a cross-sectional view of a probe assembly 12 according to another embodiment. In this embodiment, a removable stylet 100 is provided inside the lumen 62 of the elongate tubular member 60. The stylet 100 may be dimension such that it frictionally engages with the inner surface of the elongate tubular member 60. The stylet 100 may be removed from the elongate tubular member 60 by pulling the stylet 100 proximally in the direction of arrow B in FIG. 7. The stylet 100 is located within the elongate tubular member 60 when the probe assembly 12 is advanced to the tissue region of interest. The presence of the stylet 100 within the elongate tubular member 60 prevents tissue coring and plugging up the lumen 62 of the elongate tubular member 60. The stylet 100 also prevents retrograde or back flow of bodily fluids/blood from the target site. The stylet 100 may be removed prior to application of RF energy so an access passageway exists (lumen 62) to release gaseous vapor generated during the ablation process. Alternatively, the stylet 100 may be removed during the ablation process. For example, the stylet 100 may be removed during the early phase of ablation to minimize blood back-flow and solidity the tissue around the tip of the device 10. Generally, gas build-up does not happen in the early stages of the ablation process. Rather, gas build-up typically occurs near the middle and end stages of the ablation process.

The stylet 100 may include an expanding member located at the distal end that aids in preventing retrograde or back flow of bodily fluids/blood from the target site. The expanding member may include a basket or flared portion (not shown) that is expanded by a proximal pulling force and/or torsional force applied to the stylet 100. Once the tissue around the tip of the device 10 has solidified by desiccation, the stylet 100 may be removed for venting as the ablation process continues.

FIG. 8 illustrates a cross-sectional view of the cannula 18 taken along the line 8-8' of FIG. 7. The stylet 100 is shown positioned within the lumen 62 of the elongate tubular member 60. The stylet 100 may be formed from a solid needle, for example, metallic material. The stylet 100 and/or the interior surface of the elongate tubular member 60 may be coated with a lubricious coating to aid in retraction of the stylet 100 from the probe assembly 12.

Figure 9:
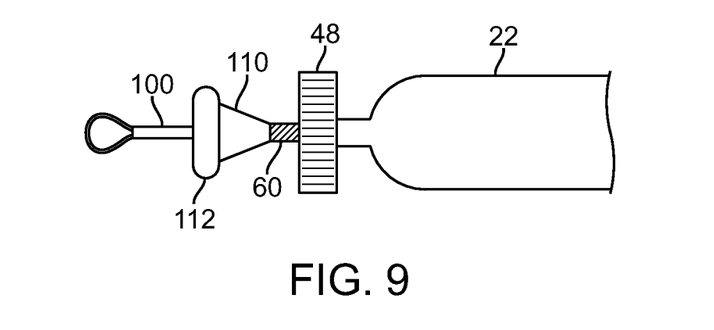
FIG. 9 is a cross-sectional view of a proximal end of a probe assembly according to one embodiment of the invention.

FIG. 9 illustrates the proximal portion of a RF probe assembly 12 according to another embodiment of the invention. In this embodiment, a locking member 110 is disposed on the proximal end 64 of the elongate tubular member 60 and is used to releasably secure the stylet 100 relative to the elongate tubular member 60. For example, the locking member 110 may include a cap portion 112 that, when tightened, securely fastens the stylet 100 to the elongate tubular member 60. When the cap portion 112 is un-tightened, the stylet 100 is slidable relative to the elongate tubular member 60. The locking member 110 may include, for instance, a Luer lock.

While the primary benefit of the elongate tubular member 60 is the ability to vent or shunt gaseous water vapor outside of the tumor there are a number of other benefits that the elongate tubular member 60 provides. For example, the elongate tubular member 60 and its corresponding lumen 62 may be used as a passageway for fluids that are delivered to the target site. For example, fluids containing a contrast agent, drugs, saline, or alcohol may be used to enhance visibility, promote ablations, and accelerate cellular death. The elongate tubular member 60 and the lumen 62 may be used to guide a working tool (e.g., biopsy tool) that can then be used to withdraw a biopsy sample for review and analysis. The lumen 62 may likewise be configured to permit passage of a guiding needle to facility placement of the probe assembly 12. For example, a narrow-diameter wire-like needle by be introduced to the target location (e.g., tumor mass). Once the wire-like needle is positioned, the probe assembly 12 may be introduced over the wire and guided into the correct position.

Figure 10:
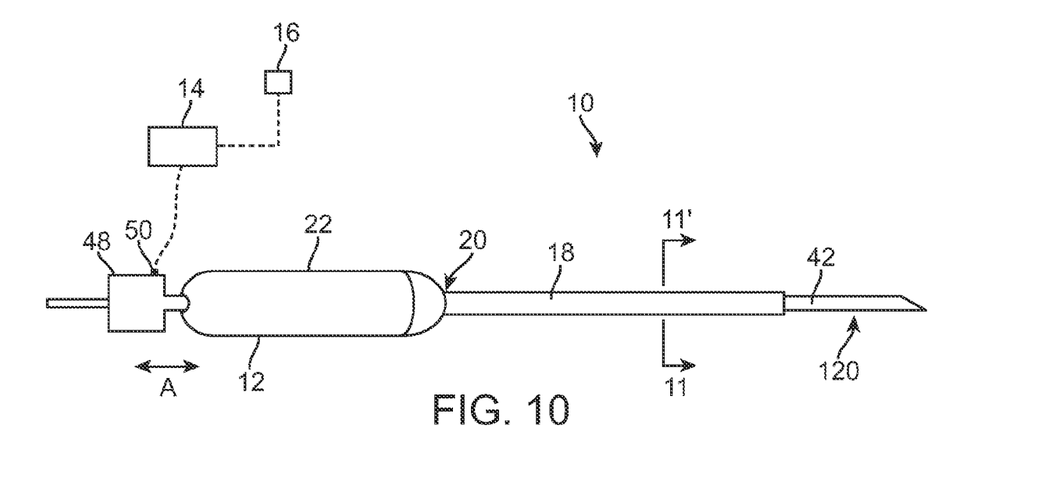
FIG. 10 is a schematic representation of a tissue ablation system according to another aspect of the invention.
Figure 11:
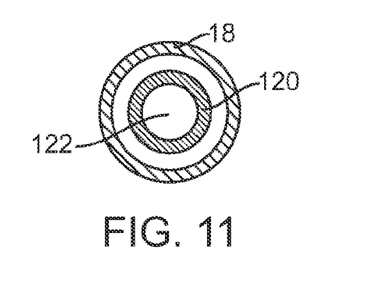
FIG. 11 is a cross-sectional view of the cannula taken along the line of 11-11' of FIG. 10.

FIG. 10 illustrates another embodiment of an RF ablation device 10. In this embodiment, the electrode member 42 may comprise a single elongate member or cannula without any associated electrode tines. For example, the electrode member 42 may be configured as a needle cannula 120. The needle cannula 120 is slidable within the elongate cannula 18 via manipulation of the hub 18. The needle cannula 120 includes a lumen 122 (as seen in FIG. 11) therein that is used to evacuate excess pressure buildup within the tumor or other diseased tissue. The lumen 122 may be dimensioned such that a stylet 100 or the like may be slidable therein.

FIG. 12 illustrates another embodiment of a RF ablation device 10. In this embodiment, no secondary venting tube (e.g., elongate tubular member 60) is used. Rather, the electrode member 42 itself includes a lumen 126 that serves to evacuate excess pressure that builds during tumor ablation. This embodiment eliminates the need to have a separate tubular element disposed within the elongate cannula 18. The electrode member 42 may include tubular member that has a plurality of electrode tines 44 disposed at the distal end. In addition, FIG. 12 also illustrates an embodiment in which the venting channel (e.g., electrode member 42) has a portion in a non-straight configuration. For example, in the handle 22, the electrode member 42 is curved to create a drip point or loop 128. This allows the steam or water vapor to condense into a reservoir contained within the handle 22. The reservoir may include a chamber, depression, or other cavity where fluid may be stored. The fluid may be evacuated if the reservoir becomes full. In addition, with reference to FIG. 12, if a stylet 100 is used in this embodiment, the stylet 100 is formed from a flexible material.

While embodiments of the present invention have been shown and described, various modifications may be made without departing from the scope of the present invention. The invention, therefore, should not be limited, except to the following claims, and their equivalents.

What is claimed is:

1. A radiofrequency ablation device comprising:
an elongate cannula having a distal portion and a proximal portion and a lumen extending between the distal portion and the proximal portion;
an elongate tubular member disposed within the lumen of the elongate cannula, the elongate tubular member having a distal region and a proximal region, the elongate tubular member including a lumen extending between the distal portion and the proximal portion thereof; and
an electrode member slidably disposed in the elongate cannula lumen, the electrode member including a plurality of tines at a distal portion thereof, the plurality of tines being configured to deploy from the elongate cannula as the electrode member is moved toward the distal portion of the elongate cannula, the electrode member further including a proximal portion and a lumen extending between the distal portion and the proximal portion,
wherein the elongate tubular member is axially fixed relative to the electrode member, and
wherein the elongate tubular member is disposed within the lumen of the electrode member and a substantial length of an outer surface of the elongate tubular member engages a substantial length of an inner surface of the lumen of the electrode member, and wherein the elongate tubular member is fixed to the electrode member by a bonding layer disposed between the elongate tubular member and the electrode member.

2. The device of claim 1, further comprising a RF energy source operatively coupled to the electrode member.

3. The device of claim 1, wherein the elongate tubular member is one of straight, angled, or curved.

4. The device of claim 1, wherein the elongate tubular member comprises a metallic tube.

5. The device of claim 1, wherein the elongate tubular member comprises a composite material.

6. The device of claim 1, wherein the proximal portion of the electrode member extends proximally with respect to the elongate cannula and terminates in a hub.

7. The device of claim 1, further comprising a vacuum source connected to the elongate tubular member.

8. The device of claim 1, further comprising a filter configured to filter material passing through the lumen of the elongate tubular member.

9. The device of claim 8, wherein the filter is disposed inside the lumen of the elongate tubular member.

10. The device of claim 1, further comprising a container configured to capture at least a portion of the material passing through the lumen of the elongate tubular member.

11. The device of claim 1, further comprising a stylet slidably disposed within the lumen of the elongate tubular member.

12. The device of claim 11, further comprising a locking member configured to lock the stylet with respect to the elongate tubular member.

* * * * *